US00PP32264P2

(12) United States Plant Patent
Hansen

(10) Patent No.: US PP32,264 P2
(45) Date of Patent: Sep. 29, 2020

(54) ***SALVIA* PLANT NAMED 'VANITY FLAIR'**

(50) Latin Name: ***Salvia pratensis* hybrid**
Varietal Denomination: Vanity Flair

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/873,096

(22) Filed: Jan. 30, 2020

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./263.1, 475
See application file for complete search history.

*Primary Examiner* — Susan McCormick Ewoldt
*Assistant Examiner* — Karen M Redden

(57) ABSTRACT

The new and distinct cultivar of perennial *Salvia* plant named 'Vanity Flair' characterized by its large, soft lavender flowers from light buds, densely arranged in verticils. The new plant has a medium to tall height, compact, rounded habit with stiff, upright, heavily-branched stems and a strong vigorous growth rate and dark gray-green foliage. 'Vanity Flair' is useful for landscaping as a specimen plant or en masse.

1 Drawing Sheet

Botanical denomination: *Salvia pratensis* hybrid.
Cultivar designation: 'Vanity Flair'.

STATEMENT REGARDING PRIOR DISCLOSURES UNDER 37 CFR 1.77(B)(6)

The first non-enabling disclosure, in the form of a catalog with a photograph and brief description was on Sep. 1, 2019 maintained by Gootjes-Allplant BV in The Netherlands. Gootjes-Allplant BV obtained their plants and all information about the new plant indirectly from the inventor. No plants of *Salvia* 'Vanity Flair' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Vanity Flair' or as the new plant. The new plant was selected from a cross under the direction of the inventor on Jun. 20, 2015 between 'Crystal Blue' U.S. Plant Pat. No. 26,344 as the female or seed parent and 'Azure Snow' U.S. Plant Pat. No. 30,534 as the male or pollen parent. The cross was performed within the breeding area of a wholesale perennial nursery in Zeeland, Mich., USA. Seed was collected in July of 2015 and sown at the same nursery. The new plant was initially evaluated in the summer of 2017 and assigned the breeder code 15-25-3 through the trial process prior to assigning the cultivar name.

The new *Salvia* was further evaluated and asexually propagated initially by division and later by basal cuttings taken at the same nursery in Zeeland, Mich., USA in 2017. Evaluation of these and further cutting grown plants shows that *Salvia* 'Vanity Flair' continues to be stable and produce true to type plants in successive generations of asexual propagation.

SUMMARY OF THE INVENTION

Plants of *Salvia* 'Vanity Flair' have not been observed under all possible environmental conditions. The phenotype may vary somewhat with variations in environment such as temperature, nutrition and light intensity without, however, any variance in genotype.

*Salvia* 'Vanity Flair' can be closely compared to *Salvia* 'Perfect Profusion' U.S. Plant Pat. No. 31,434, 'Sal Card 07' U.S. Plant Pat. No. 20,184, 'Bumblesky' U.S. Plant Pat. No. 30,085, 'Sky Dance' (not patented). 'Perfect Profusion' has a similar size with flowers of a similar coloration but the flowers and buds are much smaller. 'Sal Card 07' has a much larger habit with flowers that are darker violet-blue. 'Bumblesky' is shorter in habit smaller flowers and buds. 'Sky Dance' is a seed strain with the general traits being less branched, fewer flowers per verticil and verticils being more distantly spaced. 'Crystal Blue' has slightly shorter habit and flowers and buds are much smaller. 'Azure Snow' has two-tone deep violet-blue and white flowers.

The following characteristics in combination distinguish *Salvia* 'Vanity Flair' as a new and distinct cultivar from all other cultivars known to the inventor:

1. Large, soft lavender flowers densely arranged in verticils;
2. Stiff, upright, tightly and heavily-branched stems;
3. Light violet flower buds;
4. Medium to tall height, dense, rounded, strong, vigorous and winter-hardy habit;
5. Rugose, dark, gray-green foliage.

BRIEF DESCRIPTION OF THE DRAWINGS

The photographs of the new plant demonstrate the unique traits and the overall appearance of *Salvia* 'Vanity Flair'.

The colors are as accurate as reasonably possible with color reproductions. Variation in ambient light spectrum, source and direction may cause the appearance of minor variation in color. The plant used in the photographs was a three-year-old plant grown in an open, full-sun trial garden at a wholesale perennial nursery in Zeeland, Mich. with supplemental water and fertilizer when needed.

DETAILED BOTANICAL DESCRIPTION

Figure 1:
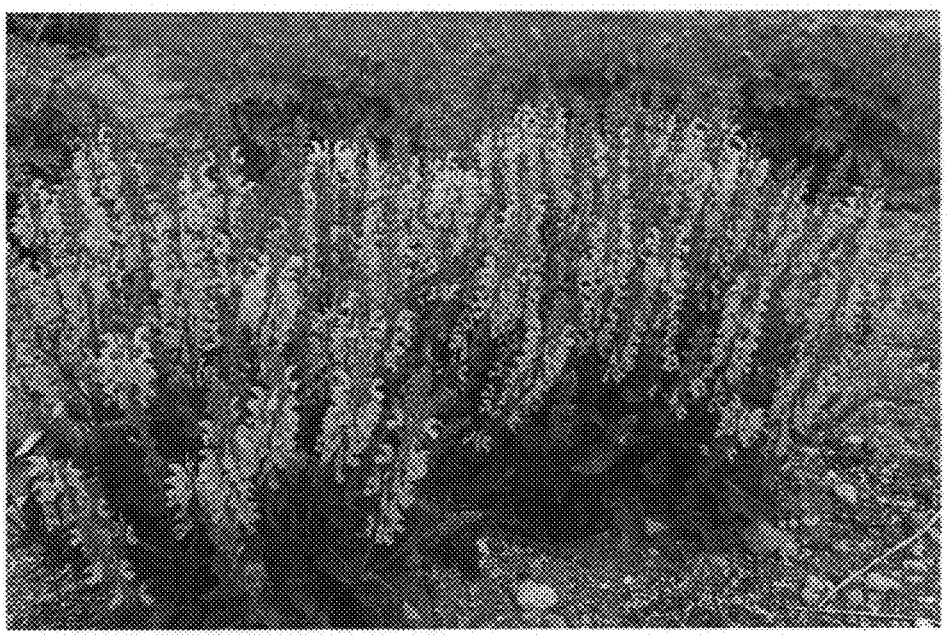
FIG. 1 shows the plant habit in full flower in a landscape.
Figure 2:
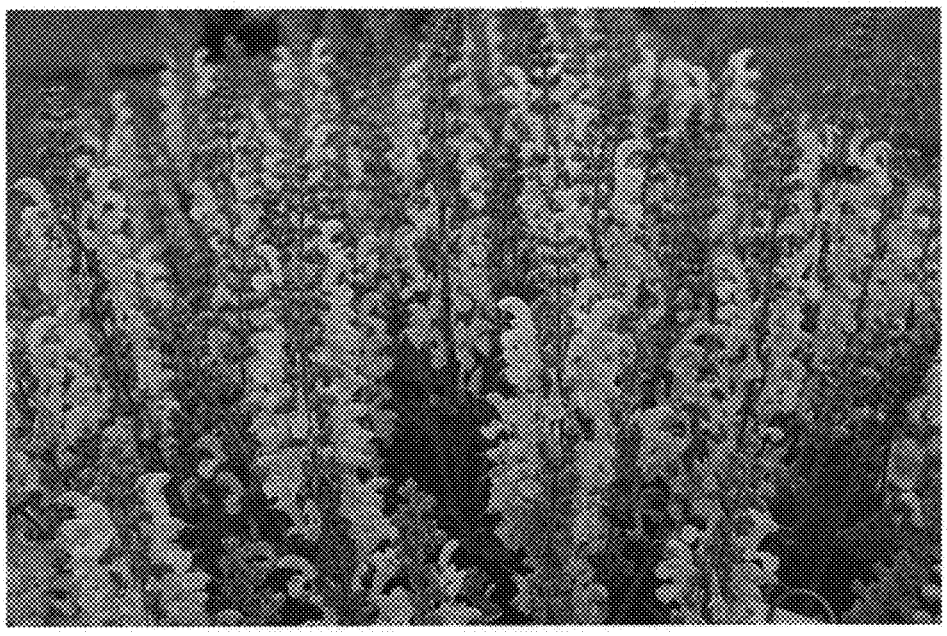
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Vanity Flair' has not been observed under all possible environments. The phenotype may vary slightly with different growing environments such as temperature, light, fertility, soil pH, moisture and plant maturity levels, but without any change in the genotype. The following observations and size descriptions are based on two-year-old plants growing in an outdoor full-sun trial garden and greenhouse-forced two-year-old plants at a wholesale perennial nursery in Zeeland, Mich. Plants were given supplemental water and fertilizer and plant growth regulators were used for the greenhouse trials only.

Botanical classification: *Salvia pratensis* hybrid;

Parentage: Female or seed parent is 'Crystal Blue'; male or pollen parent is 'Azure Snow';

Plant habit: Winter-hardy herbaceous perennial; multi-stemmed; dense; upright; with mostly basal foliage, and flowers in several tightly arranged verticils on branched upright racemes displayed above foliage; in flower with panicles about 52 cm tall and about 40 cm wide at the fullest point; cauline foliage extends up the stems about 22 cm; about 18 flowering panicles per plant;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color;

Foliage: Opposite; simple; slightly rugose; lanceolate; margin irregularly crenate and micro-ciliolate; adaxial sparsely puberulent, and abaxial pubescent; acute apex and base cordate; leaf blades to about 12.0 cm long and 4.5 cm across, decreasing in size distally; average about 8.0 cm long and 3.0 cm across; faint sage fragrance;

Foliage color: Young adaxial and abaxial between RHS 138A and RHS 138B; mature adaxial between RHS 137A and RHS 137B, mature abaxial nearest RHS 137C;

Venation: Reticulate; impressed on adaxial side and costate on abaxial side; puberulent adaxial, abaxial pubescent;

Vein color: Adaxial midrib between RHS 146D and RHS 147D, adaxial primary and secondary veins nearest 148C; abaxial midrib between RHS 145A and RHS 146D, abaxial primary and secondary veins nearest RHS 148C;

Petiole: Slightly concavo-convex; pubescent adaxial and abaxial and ciliolate margin; to about 7.0 cm long and 5.0 mm wide at base decreasing distally, average 6.0 cm long and 4.5 mm wide at base;

Petiole color: Adaxial center portion nearest RHS 146D and laterally nearest RHS 148C; abaxial midrib between RHS 145A and RHS 146D, laterally nearest RHS 148C;

Flower description: Perfect; bilabiate; zygomorphic; fused corolla portion glabrous adaxial and puberulent abaxial;

Flower size: 25.0 mm long to tip of exserted stigma, 16.0 mm tall, 6.0 mm wide; corolla 21.0 mm long, 16.0 mm tall; corolla fused basal portion 9.0 mm long, 6.0 mm tall and 4.0 mm wide;

Inflorescence: Panicle; branched at about 60° angle above horizontal, rarely compound branched; branches to 20 cm long and 3.5 mm across base; flowering portion 23 cm tall and 14 cm across; verticillate with flowering generally beginning at lower verticils and advancing up the scape, but not all flowers at each verticil opening at the same time giving the effect of a scape being in continuous flower for longer periods; typically six flowers per verticil; average distance between verticils about 15.0 mm, greater proximally and less distally; about 13 verticils per plant; about 200 to 300 flowers per panicle;

Flowering period: Flowering beginning late spring for about six weeks and repeating if initial inflorescences removed;

Peduncle: Quadrangular; pubescent to glandular; to 23.0 cm long and 5.0 mm across at base;

Peduncle color: Proximal portion nearest RHS 146C and distal portion nearest RHS 189A;

Flower attitude: Mostly horizontal, slightly upwardly, labium slightly above horizontal;

Flower longevity: About four days on the plant or as cut flower; self-cleaning, petals not persistent;

Flower fragrance: None detected under present growing conditions;

Flower buds one day prior to anthesis: Obovoid, slightly falcate; flat ventrally and flattened slightly laterally; with rounded apex; pubescent; about 15.0 mm long, 7.0 mm tall and 3.0 mm wide;

Bud color: Exposed petals along dorsal arc nearest RHS 91A, ventral nearest RHS 91B and near center between RHS 91A and RHS 91B; abaxial calyx nearest RHS 145D with veins nearest RHS 137B;

Petals: Bilabiate corolla; upper hood lip and lower lip (labium) with three lobes; glandular abaxial and glabrous adaxial;

Hood (upper) petal: Glandular abaxial, glabrous adaxial; falcate; folded along longitudinal axis; apex rounded and emarginate, with 1 mm deep notched apex and base fused with labium in proximal 9.0 mm; about 21.0 mm long, 6.0 mm tall and 1.5 mm across in folded distal portion;

Hood color: Adaxial nearest RHS 92D; abaxial between RHS 91B and RHS 91C;

Labium (lower) petal: Consisting of three lobes, two proximal side lobes and larger center lobe; side lobes glabrous adaxial and abaxial, center lobe glabrous adaxial and abaxial;

*Center lobe*.—Obcordate; cupped; truncate emarginate apex with notch about 1.0 mm deep; margin crenulate; size about 17.0 mm long (including fuse base) extending 8 mm beyond fusion point; natural width 7.0 mm and when spread to 11.0 mm.

*Center lobe color*.—Adaxial between RHS 91B and RHS 91C; abaxial nearest RHS 91A near center and near margin nearest RHS 91C.

*Fused corolla color*.—Adaxial between RHS NN155D and RHS 91D, abaxial lighter than blend between RHS 91D, RHS 92D and RHS NN155D.

*Side lobes*.—Ovate to lanceolate; apices rounded; base fused to corolla tube; mostly flat; size about 5.0 mm long from fusion and 2.0 mm wide.

*Side lobes color*.—Nearest RHS 91C adaxial and abaxial.

Androecium: Two; fused with labium, arcuate along inside upper hood petal except when triggered by pollinator;

*Filament*.—Glabrous, fused about 9.0 mm from base of labium petal; arcuate around inside of hood petal; about 15.0 mm long and 0.5 mm diameter with a 2.0 mm long trip by 1.0 mm across mechanism longitudinally folded at base; color of filament nearest RHS NN155D; color of trip mechanism between RHS 85C near center and RHS 85D.

*Anther*.—Glabrous; oblong ellipsoidal; dorsifixed; longitudinal; about 2.5 mm long and 1.0 mm diameter; color nearest RHS 165B.

*Pollen*.—Abundant; less than 0.1 mm circumference; color nearest RHS 9B.

Gynoecium: one, arcuate around inside of hood petal;

*Style*.—Exserted; about 24.0 mm long and 0.5 mm diameter; color nearest RHS NN155D at base, transitioning distally to a blend between RHS NN155D and RHS N87D.

*Stigma*.—Bifurcate and curved in the terminal 2.0 mm; about 0.3 mm diameter; apex acute; color nearest RHS N87C.

*Ovary*.—Superior; up to four-seeded; color between RHS 162A and RHS 163B.

Fruit: Nutlet, one to four per flower; globose; about 1.5 mm diameter; color nearest RHS 200A;

Calyx: Campanulate; fused in basal 7.5 mm; tube about 8.0 mm long and 8.0 mm tall at mouth and 5.0 mm wide; lower set bifurcate in distal 0.5 mm; upper set of trifurcate slightly folded in middle in distal 0.5 mm; glandular abaxial and glabrous adaxial;

Sepals: Five, three upper and two lower; linear; acute apex; 8.0 mm long, 2.5 mm across at fusion and fused in basal 7.5 mm;

Sepal color: Adaxial proximal 3 mm nearest RHS 145D with veins nearest RHS 137C, distal portion nearest RHS 137B; abaxial nearest RHS 146D, with veins of nearest RHS 138A;

Bracts: Each verticil and branch subtended by two opposite deltoid bracts; apex narrowly acute; base sessile, truncate, clasping; margin crenate; glabrous adaxial and pubescent abaxial; bract size up to 5.0 cm long and 2.5 cm wide, decreasing distally;

Bract color: Adaxial and abaxial between RHS 137A and RHS 137B with midrib nearest RHS 145D;

Pedicels: Cylindrical; puberulent to glandular; about 1.0 to 2.0 mm long and 1.0 mm diameter; curving outwardly;

Pedicel color: Nearest RHS 145A;

Culture: Plants of *Salvia* 'Vanity Flair' perform best with adequate moisture and good drainage and are hardy from USDA zone 3 to 8.

Disease and pest resistance: Resistant to diseases and pests beyond that common to *Salvia* has not been noted.

It is claimed:

1. The new and distinct perennial *Salvia* plant named 'Vanity Flair' as herein described and illustrated.

* * * * *